United States Patent [19]
Kikuta et al.

[11] Patent Number: 5,990,191
[45] Date of Patent: Nov. 23, 1999

[54] GRANULAR CARRIER FOR IMMOBILIZING MICROBIAL CELLS AND APPARATUS FOR PRODUCING THE GRANULAR CARRIER

[75] Inventors: Makoto Kikuta, Yokohama; Hitoshi Izumida; Kiyoshi Nanishi, both of Hiratsuka; Toshirou Hirama, Fujisawa, all of Japan

[73] Assignee: Kansai Paint Co., Ltd., Hyogo, Japan

[21] Appl. No.: 09/077,330

[22] PCT Filed: Nov. 22, 1996

[86] PCT No.: PCT/JP96/03439

§ 371 Date: May 27, 1998

§ 102(e) Date: May 27, 1998

[87] PCT Pub. No.: WO97/19978

PCT Pub. Date: Jun. 5, 1997

[30] Foreign Application Priority Data

Nov. 28, 1995 [JP] Japan ................................. 7-331223
Jul. 31, 1996 [JP] Japan ................................. 8-216920

[51] Int. Cl.$^6$ .............................. C08J 3/14; C12N 11/04
[52] U.S. Cl. ................................. 522/87; 522/88; 522/89; 422/232; 422/233
[58] Field of Search ................................. 522/87, 88, 89; 422/232, 233; 435/174, 177, 178, 180, 181; 530/813, 815, 816

[56] References Cited

U.S. PATENT DOCUMENTS 4,195,129  3/1980  Fukui et al. ............................ 435/182
4,605,622  8/1986  Hasegawa et al. ..................... 435/182

FOREIGN PATENT DOCUMENTS 55-40       1/1980   Japan .
55-20676    6/1980   Japan .
60-106836   6/1985   Japan .
62-19837    5/1987   Japan .
1-118529    5/1989   Japan .

*Primary Examiner*—Nathan M. Nutter
*Attorney, Agent, or Firm*—Wenderoth, Lind & Ponack, L.L.P.

[57] ABSTRACT

A microorganism cells-immobilizing granular carrier and its manufacturing system.

Said microorganism cells-immobilizing granular carrier, which has a specific gravity of 1.00 to 1.20, and which has a contact angle of 2° to 30° formed between the carrier surface and n-paraffin, and which has a surface suitable for the attachment of a microorganism, is obtained by dripping a liquid composition containing a hydrophilic photo-curable resin having (a) at least two ethylenically-unsaturated bonds in one molecule, (b) photopolymerization initiator, and (c) water-soluble macromolecular polysaccharide capable of gelatinizing through contact with alkaline metal ions or polyvalent metal ions, into an aqueous medium containing alkaline metal ions or polyvalent metal ions to gelatinize the composition; and irradiating the composition with ultraviolet radiation so as to harden said composition.

15 Claims, 6 Drawing Sheets

GRANULAR CARRIER FOR IMMOBILIZING MICROBIAL CELLS AND APPARATUS FOR PRODUCING THE GRANULAR CARRIER

CROSS-REFERENCE

This application is a 371 application of PCT/JP96/03439, filed Nov. 22, 1996.

TECHNICAL FIELD

The present invention relates to a granular carrier for immobilizing microorganism cells and a device for producing said granular carrier, more particularly to a granular carrier for immobilizing microorganism cells, which makes it possible to easily adhere and immobilize microorganism cells onto the surface of a carrier by adding the granular carrier for immobilizing microorganism cells into a microorganism suspension and then activating the microorganism cells, and a device for producing said granular carrier.

BACKGROUND ART

Immobilized microorganisms have been noticed in recent years because they may be used to realize efficient continuous fermentation in a bioreactor.

Many methods, including the entrapment method and physical adsorption method, have been known to date as microorganism immobilizing methods. Immobilization of a microorganism by the entrapment method, however, has a problem in that the cost greatly increases because it requires a complicated operation of wrapping a previously-cultured microorganism suspension in a macromolecular gel.

The physical adsorption method makes it possible to immobilize a microorganism merely by introducing a carrier into a microorganism suspension. Therefore, the method has an advantage in that the operation of entrapping a microorganism performed in the entrapment method is not necessary. Carriers such as activated carbon, porous glass, sellite, chitin, and cellulose are known as carriers used for the physical adsorption method.

However, because surface structures of these carriers are not suitable for attachment of microorganisms, there is a problem in that only a small number of microorganisms are attached, and there is a disadvantage in that it is difficult to cause a flow in a fermenter or bioreactor, depending on the type of carrier, because of its high specific gravity.

It is the first object of the present invention to provide a granular carrier for immobilizing microorganism cells, whose surface structure is suitable for attachment of a microorganism and whose specific gravity ranges between 1.00 and 1.20, and which does not lower the flowability in a fermenter or bioreactor.

Moreover, a device for manufacturing the above granular carrier is disclosed in, for example, the official gazette of Japanese Patent Laid-Open No. Hei 1-118529. According to the system disclosed in this official gazette, dripped granular gels are put in a Petri dish so that grains are lined up, and they are irradiated with ultraviolet radiation by a high-pressure mercury lamp while being vibrated.

Though this system realizes irradiation at a certain light intensity, it has a problem in that the production efficiency is very low because continuous production is impossible.

Moreover, the present inventor previously proposed a device for manufacturing grains by moving dripped granular gels by a transparent spiral tube and simultaneously irradiating the gels with active rays (official gazette of Japanese Patent Laid-Open No. Sho 60-106836).

Figure 1:
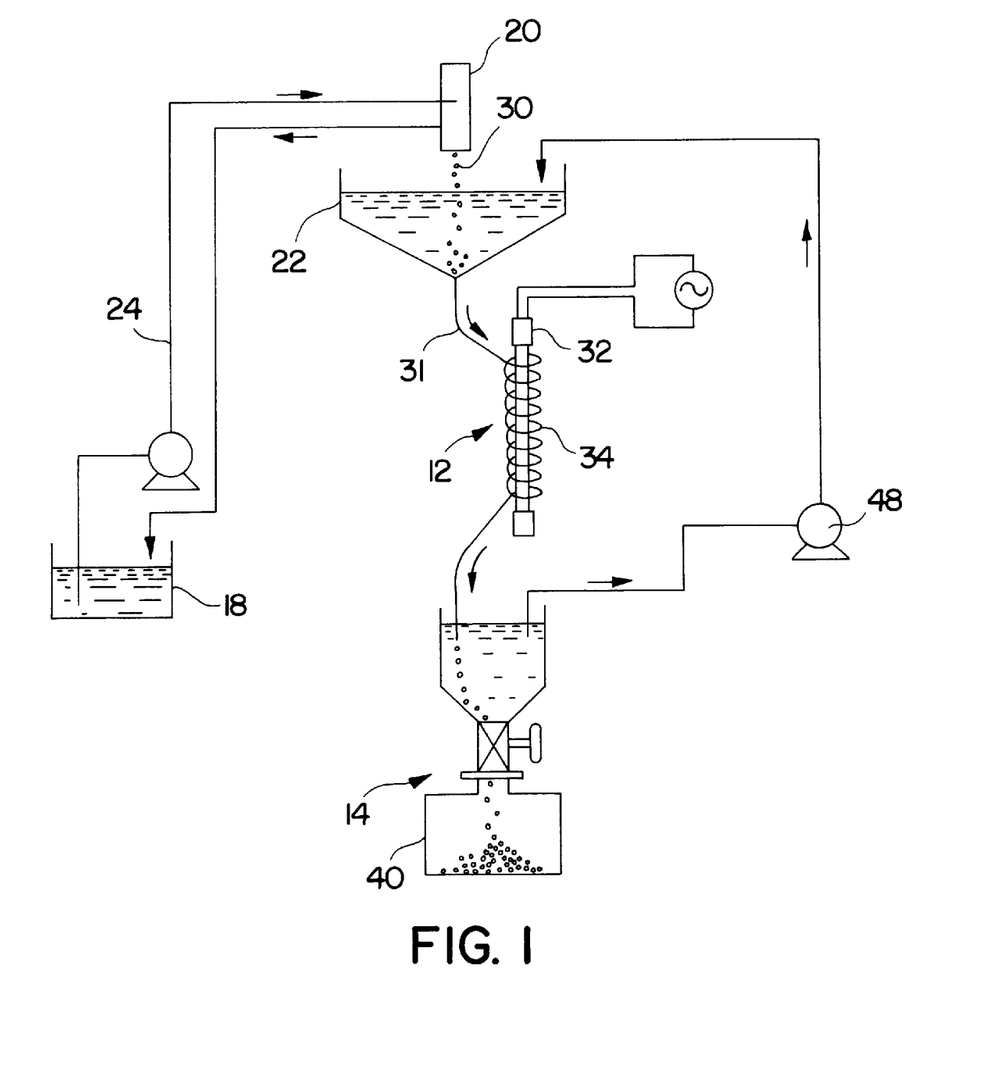
FIG. 1 is a schematic front view of a conventional particulate matter manufacturing system.

The previously proposed system is described below by referring to FIG. 1. This system comprises a tank 18 for storing a liquid composition containing a photo-curable resin, polymerization initiator, and water-soluble polysaccharide capable of gelatinizing, a dripping unit 20 for dripping the liquid composition through a nozzle, and a gelatinizing vessel 22 for storing an aqueous medium containing polyvalent metal ions.

The liquid composition is supplied to the dripping unit 20 from the tank 18 through a transport tube 24. The dripping unit 20 stores a predetermined amount of liquid composition and has a nozzle 30 at the lower position so as to drip the liquid composition from the front end of the nozzle. A droplet of the liquid composition drops into the aqueous medium containing the polyvalent metal ion stored in the gelatinizing vessel 22 and is gelatinized, and, thereafter, is supplied to a light irradiation section 12 through a tube 31 connected to the bottom of the gelatinizing vessel 22.

When a liquid gel descends through a spiral transparent tube 34 together with the aqueous medium, it is irradiated with active rays emitted from an adjacently-arranged light source 32, and a photo-curable resin in particulate matter causes an optical reaction. The particulate matter, which has increased in strength due to the optical reaction, moves to a grain recovery section 14 and is stored in a recovery vessel. The aqueous medium is returned to the gelatinizing vessel 22 by a pump 48 and is repeatedly used.

This particulate matter-manufacturing system has superior advantages in that it realizes continuous production and light irradiation for a relatively long time.

However, it is clear that the system has the following problems to be solved:

(a) One light source (or more) is (or are) necessary for one tube, and the production efficiency is low.

(b) Because a granular gel flows in a tube in almost a horizontal direction, the irradiation efficiency is lowered due to the screening effect because of crowded grains when there is a density difference between the a granular gel and a medium. Moreover, when the flow rate is increased to eliminate the crowdedness of grains, the tube length is increased and the system space increases.

(c) When the transparent spiral tube is made of plastic, it is inferior in durability because deterioration due to ultraviolet radiation is accelerated. When the tube is made of glass, it is not easy to handle the tube when it is increased in size and the cost increases.

(d) Because the batch system (taking out particulate matter when it is collected in the recovery vessel 40) is used, the particulate matter-ejecting operation is complex.

(e) When taking particulate matter out of the recovery vessel 40, aqueous medium is also taken out. Therefore, it is necessary to separate the particulate matter from aqueous media and to replenish the recovery vessel with aqueous medium.

In view of these problems, it is the second object of the present invention to provide a device for producing particulate matter containing a photo-curable resin as a granular carrier for immobilization, in large quantities and efficiently.

DISCLOSURE OF THE INVENTION

The present inventors repeated earnest studies in order to achieve the above objects, and have found the following as a result: It has been known that hydrogen bonds between a carrier and a microorganism or hydrophobic bonds between the hydrophobic portion of the carrier and that of the cell wall of the microorganism are related to attachment of the microorganism. The force of the hydrophobic bonds between the hydrophobic portion of the carrier and that of the cell wall of the microorganism decreases when the surface of the carrier is strongly hydrophilic, while the force of the hydrogen bonds between the carrier and the microorganism decreases when the surface of the carrier is strongly hydrophobic. Hence, a surface having a proper hydrophilic-hydrophobic balance is necessary for a microorganism to attach to the surface of a carrier. They have further found that it is possible to make the specific gravity of a carrier as low as that of water by using a synthetic resin as the carrier, and that it is also possible to easily make the specific gravity of carrier high by adding silica powder or the like having a high specific gravity to the carrier, and, thus, they have completed a granular carrier for immobilizing microorganism cells and a device for manufacturing said carrier.

Thus, the present invention provides:

a granular carrier for immobilizing microorganism cells having a surface suitable for attachment of a microorganism, characterized in that the carrier is obtained by dripping a liquid composition containing (a) a hydrophilic photo-curable resin having at least two ethylenically unsaturated bonds in one molecule, (b) photopolymerization initiator, and (c) water-soluble macromolecular polysaccharide capable of gelatinizing through contact with an alkaline metal ion or polyvalent metal ion, into an aqueous medium containing alkaline metal ions or polyvalent metal ions to gelatinize the composition, and irradiating the composition with active rays to cure it, said carrier having a specific gravity of 1.00 to 1.20, and a contact angle of 2° to 30° formed between the carrier surface and n-paraffin; and a particulate matter-manufacturing device comprising a gelatinizer for forming a granular gel by dripping a liquid composition containing (a) a hydrophilic photo-curable resin having at least two ethylenically unsaturated bonds in one molecule, (b) photopolymerization initiator, and (c) water-soluble macromolecular polysaccharide capable of gelatinizing through contact with an alkaline metal ion or polyvalent metal ion, into an aqueous medium containing alkaline metal ions or polyvalent metal ions to gelatinize the composition, and a light irradiator for forming particulate matter by irradiating a granular gel formed by the gelatinizer with ultraviolet radiation and curing the photo-curable resin in the granular gel, in which the light irradiator is provided with a light source and a plurality of transparent tubes which are almost vertically arranged closely to the light source, and in which the granular gel is moved.

The present invention is described below in greater detail.

(a) Photo-curable Resin

The present invention uses a photo-curable resin having at least two ethylenically unsaturated bonds in one molecule as one of the carriers for immobilizing microorganism cells. As the photo-curable resin, there is preferably used a resin which is capable of generally having a number average molecular weight of 300 to 30,000, preferably 500 to 20,000, and which contains enough ionic or nonionic hydrophilic groups, such as hydroxyl groups, amino groups, carboxyl groups, phosphoric acid groups, sulfonic acid groups, and ether linkages, to be uniformly dispersed in an aqueous medium and which cures and changes to water-insoluble resin when irradiated with active rays whose wavelength ranges between approx. 250 and approx. 600 nm. As this type of photo-curable resin, there can be used a resin already known as a immobilizing carrier for entrapment immobilization (refer to, for example, the official gazettes of Japanese Patent Publication Nos. Sho 55-40, Sho 55-20676, and Sho 62-19837). The following are typical substances.

(i) Compounds having a photopolymerizable ethylenically-unsaturated group at the both ends of polyalkylene glycol such as:
(1) Polyethylene glycol di(meth)acrylates obtained by esterifying hydroxyl groups at the both ends of polyethylene glycol of 1 mol having a molecular weight of 400 to 6,000 by 2 mol of (meth)acrylic acid
(2) Polypropylene glycol di(meth)acrylates obtained by esterifying hydroxyl groups at the both ends of polypropylene of 1 mol having a molecular weight of 200 to 4,000 by 2 mol of (meth)acrylic acid
(3) Unsaturated urethanized polyethylene-glycol obtained by urethanizing hydroxyl groups at the both ends of polyethylene glycol of 1 mol having a molecular weight of 400 to 6,000 by 2 mol of diisocyanate compound such as tolylene diisocyanate, xylylene diisocyanate, or isophoron diisocyanate and then, adding 2 mol of unsaturated monohydroxyethyl compound such as 2-hydroxylethyl (meth)acrylate
(4) Unsaturated urethanized polypropylene-glycol obtained by urethanizing hydroxyl groups at the both ends of polypropylene glycol of 1 mol having a molecular weight of 200 to 4,000 by 2 mol of diisocyanate compound such as tolylene diisocyanate, xylylene diisocyanate, or isophoron diisocyanate and then, adding 2 mol of unsaturated monohydroxyethyl compound such as 2-hydroxylethyl (meth)acrylate (ii) Large-acid-value unsaturated polyester resins:
Salts of unsaturated polyester having an acid value of 40 to 200 obtained by esterifying polyvalent carboxylic acid component containing unsaturated polyvalent carboxylic acid and polyvalent alcohol (iii) Large-acid-value unsaturated epoxy resins:
Unsaturated epoxy resins having an acid value of 40 to 200 obtained by adding acid anhydride to hydroxyl groups remaining in an additional reaction product between epoxy resin and unsaturated carboxyl compound such as (meth)acrylic acid (iv) Anionic unsaturated acrylic resins:
Resins obtained by introducing photopolymerizable ethylenically-unsaturated group to a copolymer containing a carboxyl group, phosphoric acid group, and/or sulfonic acid group obtained by copolymerizing at least two types of (meth)acrylic-based monomers selected out of (meth)acrylic acid and (meth)acrylic acid ester (v) Unsaturated polyamide:
Unsaturated polyamide and the like obtained by making an adduct of diisocyanate such as tolylene diisocyanate or xylylene diisocyanate and an unsaturated hydroxyl compound such as 2-hydroxyethyl acrylate additionally react on water-soluble polyamide such as gelatin The above described photo-curable resins may be used independently or in combination of two or more thereof.

Among these photo-curable resins, a compound having an photopolymerizable ethylenically-unsaturated group at the both ends of polyalkylene glycol in the above Item (1) can be particularly advantageously used for the present invention. Products with trade names of ENT-1000, ENT-2000, ENT-4000, ENTG-2000, and ENTG-3800 are typical ones sold by KANSAI PAINT CO., LTD.

(b) Photopolymerization Initiator

A photopolymerization initiator is included in a liquid composition according to the present invention in order to accelerate the photopolymerization of the photo-curable resins described above. A usable photopolymerization initiator is decomposed by irradiation with light to produce a radical and the radical causes a crosslinking reaction between resins having a polymerizable unsaturated group by serving as a polymerization initiator. For example, the following substances can be listed: $\alpha$-carbonyls such as benzoin; acyloin ethers such as benzoin ethyl ether; polycyclic aromatic compounds such as naphthol, $\alpha$-substituted acyloins such as methyl benzoin, and azoamide compounds such as 2-cyano-2-butylazoformamide.

(c) Water-soluble Macromolecular Polysaccharide

The water-soluble macromolecular polysaccharide used for the present invention is water-soluble, and can be changed to a gel that is insoluble or hardly-soluble in water when contacting polyvalent metal ions in an aqueous medium and generally has a molecular weight of approx. 3,000 to approx. 2,000,000. A water-soluble macromolecular polysaccharide is preferably used which normally shows a solubility of at least approx. 10 g/l (25° C.) under a water-soluble state before contacting polyvalent metal ions.

Water-soluble macromolecular polysaccharides having the above characteristics include the alkaline metal salts of alginic acid and carageenan.

In these water-soluble macromolecular polysaccharides, the carageenan can be changed to a gel by alkaline metal ions such as potassium ions or sodium ions, and the alkaline metal salt of alginic acid can be changed to a gel when contacting at least one type of polyvalent metal ion of the alkaline earth metal ions such as magnesium ions, calcium ions, strontium ions, and barium ions or other polyvalent metal ions such as aluminum ions, cerium ions, and nickel ions.

The concentration of alkaline metal ions or polyvalent metal ions to be gelatinized generally ranges between 0.01 and 5 mol/l, depending on the type of water-soluble macromolecular saccharide.

Liquid Composition

It is possible to change the above components (a), (b), and (c) to a liquid composition by mixing them in an aqueous medium. Water or aqueous buffer solution is preferable as a usable aqueous medium. Moreover, it is possible to use water-soluble alcohols and water-soluble ketones.

Though the mutual use rate of the above components (a), (b), and (c) is not strictly restricted, it is preferable to mix 100 parts by weight of a photo-curing resin, 0.01 to 5 parts by weight of a photopolymerization initiator, and 0.1 to 15 parts by weight of a water-soluble macromolecular saccharide.

The liquid composition obtained by the above method is formed into particulate matter by a granular carrier-manufacturing device to be described later.

In the case of thus obtained granular carrier for immobilizing microorganism cells, the surface of the carrier must have a proper hydrophilic-hydrophobic balance for a microorganism to easily attach to the carrier and this surface characteristic can be shown by a contact angle formed between the carrier surface and n-paraffin and the angle is adjusted in a range of 2° to 30°. A contact angle formed between the carrier surface and n-paraffin can be easily measured by dropping one droplet of n-paraffin onto the carrier surface and using a contact angle measuring instrument. Moreover, having specific gravity ranging from 1.00 to 1.20, the granular carriers can smoothly flow in a fermentor or bioreactor.

Furthermore, owing to the contact angle formed between the carrier surface and n-paraffin in a range of 2° to 30°, the granular carrier for immobilizing microorganism cells provides a surface to which a microorganism may easily attach but from which it is difficult to remove a microorganism.

Microorganism cells can be easily immobilized to the carrier when the carrier is put into a fermentor or bioreactor in which microorganisms are suspended to attach to the microorganisms. Moreover, it is possible to immobilize the microorganism cells to the carrier by a method of previously putting the carrier in a culture medium and seeding microorganisms and then culturing them. Furthermore, carrier may be put into an incubator to attach to microorganisms, then into a bioreactor. Though the amount of the carrier to be put in an incubator, fermentor, or bioreactor is not specified, a range between 1% by volume and 60% by volume of a culture medium is generally preferable.

Moreover, when microorganism cells are immobilized by the entrapment method, it is possible to easily obtain an immobilized granular carrier by including a microorganism cells in the liquid composition comprising the above components (a), (b), and (c). It is the most suitable to use the carrier for a fluidized-bed-type bioreactor or agitation-type fermentor. However, it is also possible to use the carrier for a fixed-bed-type bioreactor or fermentor.

In the case of a microorganism cells-immobilizing carrier of the present invention, the surface structure is suitable for attachment of a microorganism and therefore, a lot of microorganisms can be attached to the surface. The type of microorganism to be attached to the carrier is not restricted. The carrier can be used for both anaerobic and aerobic microorganisms. The following can be listed as types of microorganisms: molds such as Aspergillus, Penicillium, and Fusarium; yeasts such as Saccharomyces, Phaffia, and Candida; and bacteria such as Zymomonas, Nitrosomonas, Nitrobacter, Paracoccus, Vibrio, Methanosarcina, and Bacillas.

Because a granular carrier manufacturing system of the present invention uses a plurality of transparent tubes almost vertically arranged, a high production efficiency is obtained, the grain distribution state in the tubes is better than that in spiral tubes, and a high irradiation efficiency is obtained.

Moreover, because a particulate matter manufacturing system of the present invention has a simple straight channel, glass such as quartz glass or pyrex glass can be used and the system can be increased in size.

BEST MODE FOR CARRYING OUT THE INVENTION

Figure 2:
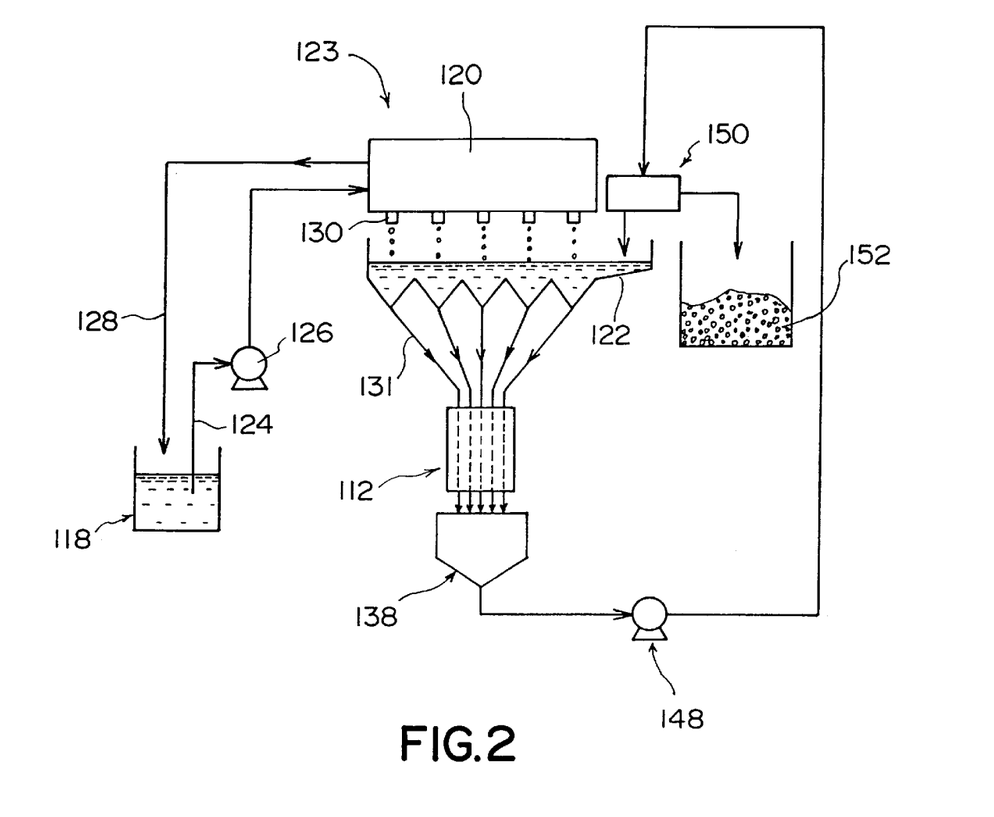
FIG. 2 is a schematic front view of a particulate matter manufacturing system of the present invention.

A granular carrier manufacturing system of a preferred embodiment of the present invention is described below by referring to FIG. 2.

The granular carrier manufacturing system comprises a tank 118 for storing a liquid composition, a gelatinizer 123 provided with a dripping unit 120 and a gelatinizing vessel 122, a light irradiator for forming particulate matter by irradiating a granular gel with ultraviolet radiation to harden it, a collection tank 138 for collecting the formed particulate matter, a circulation pump 148 for delivering particulate matter and aqueous media from the collection tank 138, a solid-liquid separator 150 for receiving particulate matter and aqueous media from the circulation pump 148 and separating the particulate matter from the aqueous media, and a recovery vessel 152 for receiving particulate matter from the solid-liquid separator 150. It is permitted to previously make the above liquid composition contain an enzyme or microorganism cells.

It is preferable that the tank 118 is provided with agitation blades (not illustrated) so as to keep liquid composition under a uniform state. The liquid composition is supplied to a dripping unit 120 from the tank 118 through a transport tube 124 and a pump 126. The dripping unit 120 holds a predetermined amount of liquid composition and extra liquid composition is returned to the tank 118 through an ejection tube 128.

The dripping unit 120 has a plurality of fine nozzles 130, for example, 5 nozzles at its lower position so that liquid composition drips from the front ends of the nozzles 130. The dripping unit is not restricted to this type. It is also possible to use a unit for spraying liquid composition from the front end of a nozzle by using the centrifugal force and a unit for dripping liquid composition from the front end of a nozzle in the form of grains by atomizing the liquid composition.

The gelatinizing vessel 122, as illustrated, is set below the dripping unit 120 to store the above aqueous media for containing alkaline metal ions or polyvalent metal ions for gelatinizing liquid composition. That is, a droplet of liquid composition formed by the dripping unit 120 and containing an enzyme or microorganism cells is dropped into the aqueous medium containing polyvalent metal ions stored in the gelatinizing vessel 122 and gelatinized. The bottom of the gelatinizing vessel 122 has recesses corresponding to the number of transparent tubes provided for the light irradiator 112 so that formed gelatinized grains are collected to the central portions of these recesses due to the gravity and the attraction of the circulation pump 148. A tube 131 is connected below the central portion of each recess of the gelatinizing vessel 122 and the gelatinized grains formed as described above are sent to the light irradiator 112.

The light irradiator 112 is provided with a light source and a transparent tube almost vertically set. Details of the light irradiator 112 are described later. Granular gels are irradiated with ultraviolet radiation emitted from a nearby light source while passing through a plurality of transparent tubes, the photo-curable resin in the granular gels causes photopolymerization, and particulate matter having high strength is manufactured.

The granular gels passing through the transparent tubes are collected in the collection tank 138 and then, pass through the circulation pump 148, and are sent to the solid-liquid separator 150.

It is preferable to us a snake pump or hose pump having an internal structure in which particulate matter is not broken as the circulation pump 148. Moreover, it is possible to constitute the circulation pump 148 so that the time for granular gels to pass through transparent tubes can be controlled by controlling the flow rate of the circulation pump 148.

Particulate matter and aqueous media are separated from each other by the solid-liquid separator 150, the particulate matter is continuously collected by the recovery vessel 152 separate from a circulation path and the aqueous media are returned to the gelatinizing vessel 122.

Therefore, because the particulate matter manufacturing system makes it possible to automatically and continuously take out particulate matter to the outside of a system, the particulate matter can be easily ejected. Moreover, because most of the aqueous media are separated from granular gels and returned to a gelatinizing vessel, it is only necessary to replenish a small amount of the aqueous media corresponding to the amount of aqueous media brought to the outside of the system because of attaching to the surface of the particulate matter and therefore, it is possible to easily replenish aqueous media.

Embodiments of light irradiators which can be used for a particulate matter manufacturing system of the present invention are described below in detail.

Figure 3A:
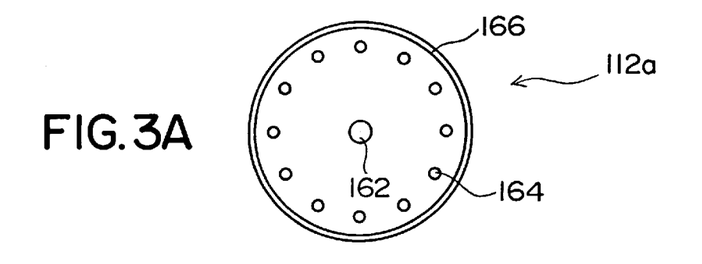
FIG. 3A is a top view of an embodiment of a light irradiator used for a particulate matter manufacturing system of the present invention and FIG. 3B is a front view showing the light irradiator a part of which is cut out.
Figure 3B:
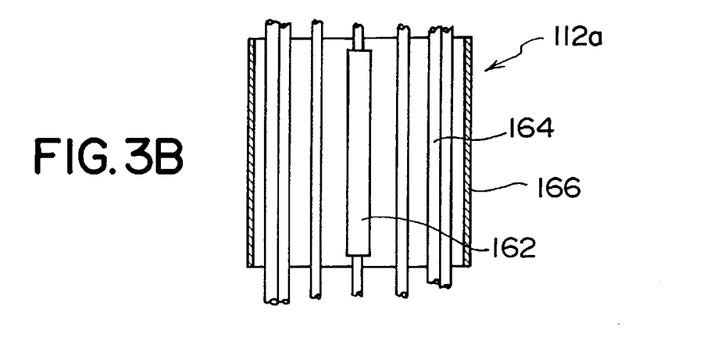

FIGS. 3A and 3B show a light irradiator 112a according to a first embodiment. FIG. 3A is a top view of the light irradiator and FIG. 3B is a front view of a reflector 166 whose center is cut out. The light irradiator 112a comprises a light source 162, 12 transparent tubes 164 arranged at equal distances so as to surround the light source 162, and the cylindrical reflector 166 located outside of the transparent tubes 164. The light energy output from the reflector 166 and light source 162 is effectively used. The top end of each transparent tube 164 is connected to the tube 131 shown in FIG. 2. The arrangement of the light source 162 and transparent tubes 164 of the light irradiator makes it possible to supply the energy output from the light source 162 to granular gels passing through the transparent tubes. It is necessary that the thickness of each transparent tube 164 has a dimension enough for a granular gel to pass through it. Moreover, it is possible to effectively use light by increasing the relative dimension of the transparent tube 164 to the light source 162 and reflector 166 and decreasing the gap.

Figure 4:
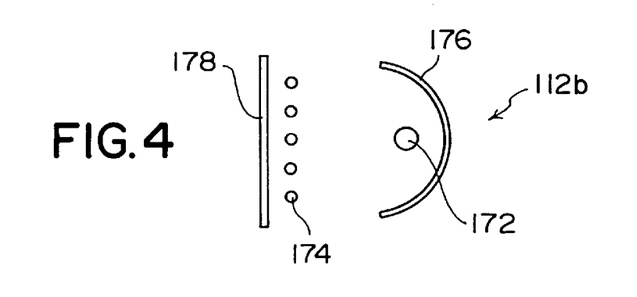
FIG. 4 is a top view of another embodiment of a light irradiator used for a particulate matter manufacturing system of the present invention.

FIG. 4 shows a top view of a light irradiator 112b according to a second embodiment. The light irradiator 112b comprises a light source 172, five transparent tubes 174 arranged in a line at equal intervals at the front of the light source 172, a semi-cylindrical reflector 176 located at the rear of the light source 172, and a flat reflector 178 located at the rear of the transparent tubes 174. The reflector 176 at the rear of the light source 172 adjusts a light intensity distribution so that the light energy output from the light source 172 is almost equally supplied to each transparent tube 174. The reflector 178 at the rear of the transparent tubes 174 realizes effective activation of light energy by reflecting the passing light. The light irradiator 112b makes it possible to adjust the distance between the light source 172 and the transparent tubes 174 and easily maintain a predetermined light intensity.

Figure 5:
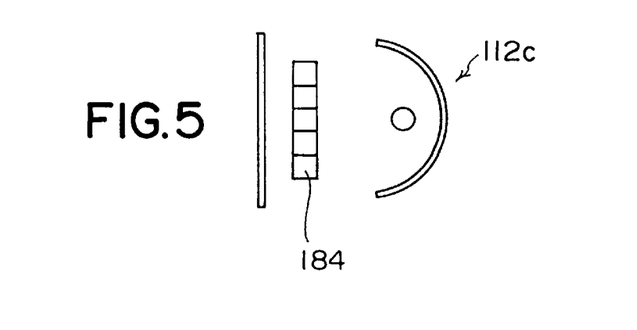
FIG. 5 is a top view of still another embodiment of a light irradiator used for a particulate matter manufacturing system of the present invention.

FIG. 5 shows a top view of a light irradiator 112c according to a third embodiment. In the case of the light irradiator 112c, as shown in FIG. 4, a transparent tube 184 is formed with a plurality of conduits by partitioning a transparent duct with a wall instead of independently arranging a plurality of transparent tubes in a line. Other structures of the light irradiator 112c are the same as those of the light irradiator 112b shown in FIG. 4. As shown in FIG. 4, when independently arranging the transparent tubes 174, a gap is formed between the transparent tubes 174 because the section of the transparent tubes 174 requires a maintaining space and therefore, the space is wasted. However, the light irradiator 112c shown in FIG. 5 does not have the waste.

Figure 6A:
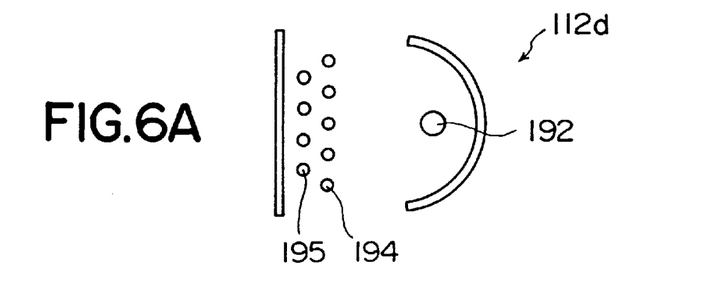
FIG. 6A is a top view of still another embodiment of a light irradiator used for a particulate matter manufacturing system of the present invention and FIG. 6B is a front view of the aspect in FIG. 6A.
Figure 6B:
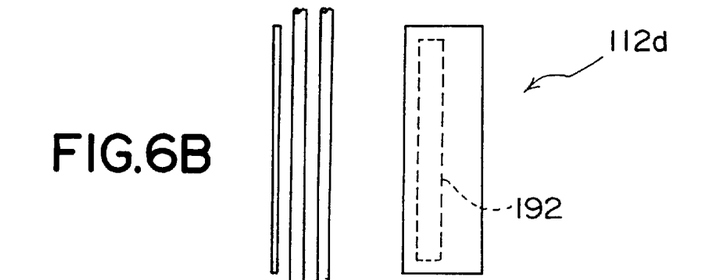

FIGS. 6A and 6B show a light irradiator 112d according to a fourth embodiment. FIG. 6A is a top view of the light irradiator and FIG. 6B is a front view of the light irradiator. The light irradiator 112d shown in FIG. 6 makes it possible to improve the productivity of particulate matter by further arranging a line of transparent tubes 195 at positions to which ultraviolet radiation is directly applied from a light source 192 through gaps between transparent tubes 194 arranged in a line to eliminate any unnecessary space.

Figure 7:
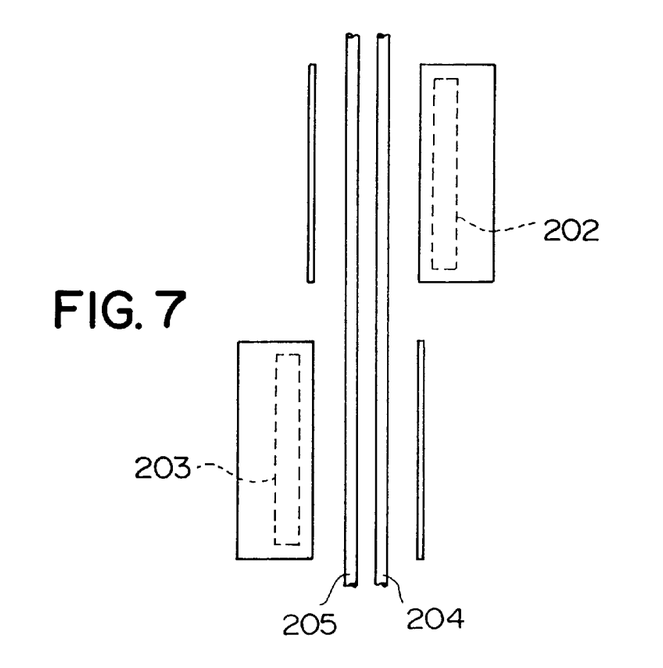
FIG. 7 is a front view of still another embodiment of a light irradiator used for a particulate matter manufacturing system of the present invention.

When arranging transparent tubes 194 and 195 in two lines as shown in FIG. 6, a difference may occur in photo-curing reactions because the light intensity is slightly weak in the case of the transparent tube 195 in the line of the position far from the light source 192 compared to the case of the transparent tube 194 in the line of the position close to the light source 192. In this case, as shown in FIG. 7, it is possible to equalize the light energy by vertically arranging a plurality of light sources 202 and 203 and setting the position of each light source alternately to transparent tubes 204 and 205. In the case of this embodiment, the particulate matter passing through the right transparent tube 204 is far from the light source at the downstream side though it is close to the light source at the upstream side.

Figure 8:
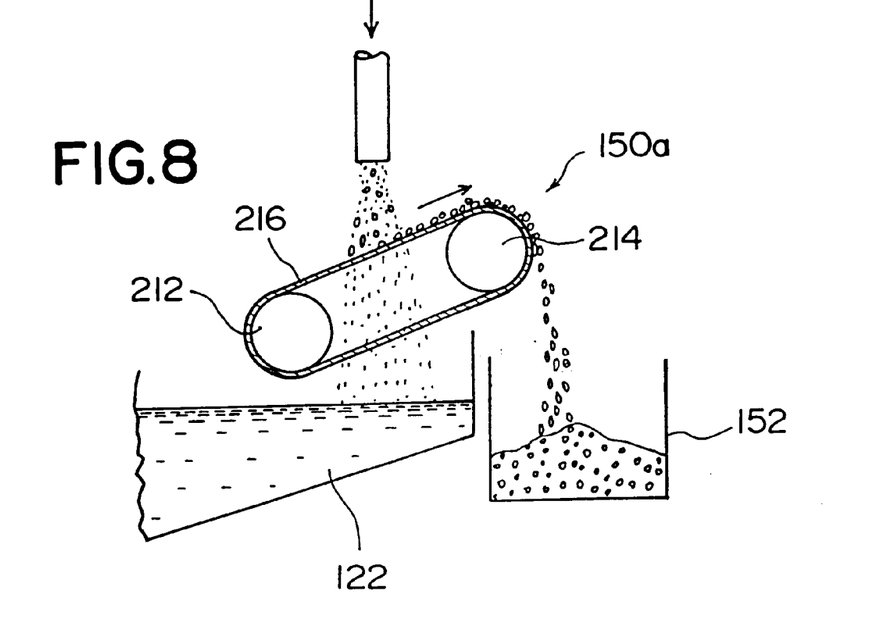
FIG. 8 is a front view of an embodiment of a solid-liquid separator used for a particulate matter manufacturing system of the present invention.

Embodiments of solid-liquid separators which can be used for a particulate matter manufacturing system of the present invention are described below by referring to FIGS. 8, 9, and 10. FIG. 8 shows a solid-liquid separator 150a of a first embodiment. The solid-liquid separator 150a comprises an endless belt 216 supported by two wheels 212 and 214. The endless belt 216 is formed with a net to support supplied particulate matter and pass an aqueous medium which is a liquid component. The endless belt 216, as shown in FIG. 8, is lowered at the gelatinizing vessel 122 side and risen at the recovery vessel 152 side, and driven so that the upper side of the endless belt 216 moves from the gelatinizing vessel 122 toward the recovery vessel 152. When particulate matter and aqueous media are supplied onto the endless belt 216 of the solid-liquid separator 150a, the particulate matter drops into the recovery vessel 152 at an end of the separator and the aqueous media pass through the endless belt 216, and they are returned to the gelatinizing vessel 122 and repeatedly used.

Figure 9:
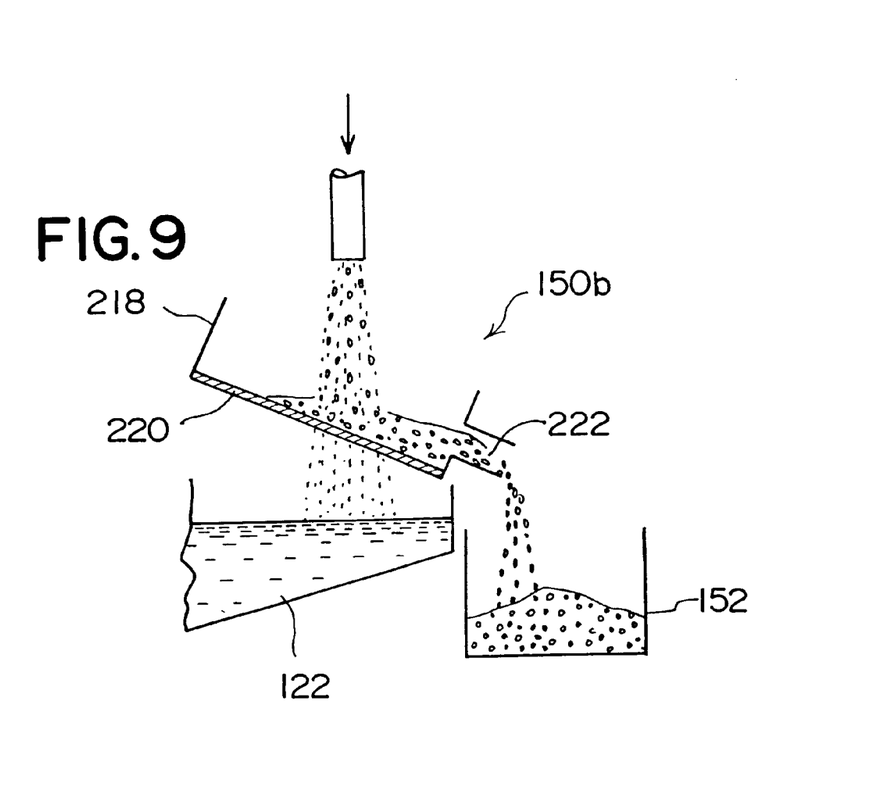
FIG. 9 is a front view of another embodiment of a solid-liquid separator used for a particulate matter manufacturing system of the present invention.

FIG. 9 shows a solid-liquid separator 150b of a second embodiment. The solid-liquid separator 150b comprises a rectangular-parallelepiped box diagonally set whose upper side is opened and whose lower side 220 is formed with a net, and in which an exit opening 222 is provided for one side located below and three other sides are formed with a flat plate respectively. In the case of the solid-liquid separator 150b, particulate matter and aqueous media are supplied from the upper-side opening onto the lower-side 220, the particulate matter slips downward by its own weight and drops to the recovery vessel 152 from the exit opening 222, and they are collected. The aqueous media are returned to the gelatinizing vessel 122 by passing through the net.

Figure 10:
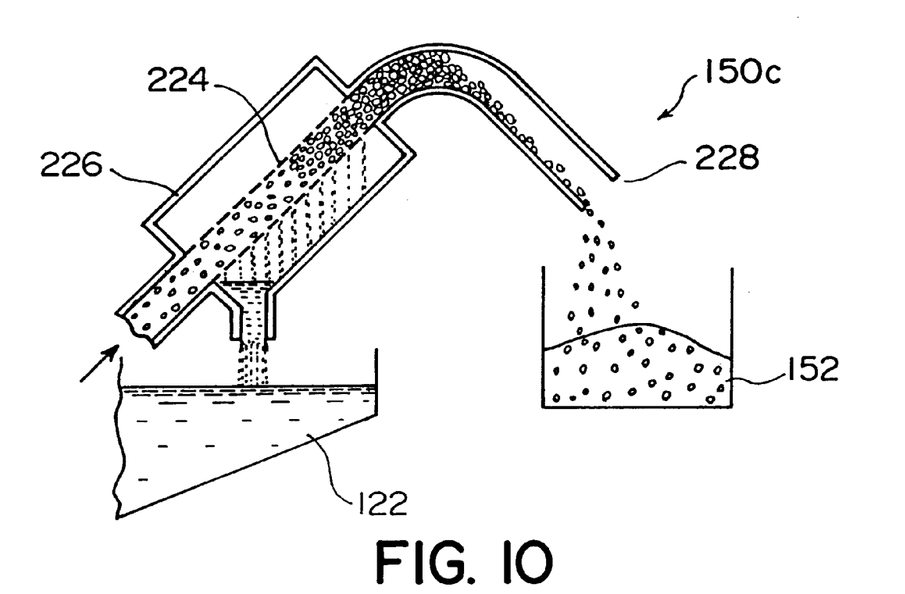
FIG. 10 is a front view of still another embodiment of a solid-liquid separator used for a particulate matter manufacturing system of the present invention.

FIG. 10 shows a solid-liquid separator 150c of a third embodiment. The solid-liquid separator 150c comprises a cylindrical net 224 provided for a part of a path for transporting the mixture of particulate matter and aqueous media and a box 226 covering the net and having an opening at its bottom. In the case of the solid-liquid separator 150c, when particulate matter and aqueous media are supplied from the lower side, the aqueous media are returned to the gelatinizing vessel from an opening 228 at the bottom of the box 22 by passing through the net while the particulate matter is pushed upward, dropped to the recovery vessel 152 from the exit opening 228, and collected.

As a method for immobilizing a microorganism or enzyme to particulate matter manufactured by the present invention, there can be employed a method of mixing manufactured particulate matter with a solution containing a microorganism or enzyme to attach the microorganism or enzyme to the surface of the particulate matter, or a method of mixing a microorganism or enzyme in a liquid composition and thereafter, manufacturing particulate matter and putting the particulate matter in the liquid composition.

EMBODIMENTS OF GRANULAR CARRIER

Embodiment 1

After completely mixing 150 g of photo-curable resin ENT-2000 (manufactured by KANSAI PAINT CO., LTD.) with 100 g of water, 10 g of benzoyl ethyl ether and 50 g of 2% sodium alginate solution are added and adequately agitated to prepare a liquid composition. Then, a granular microorganism cells-immobilizing carrier having a specific gravity of 1.01 and a contact angle formed with n-paraffin of 24° is obtained by using a manufacturing system of the present invention.

A 3% calcium chloride solution is used as an aqueous medium containing metallic ions.

Then, 100 ml of the culture medium GY-10 (comprising 1 g/l of yeast extract and 100 g/l of glucose) is added to a 500-ml Erlenmeyer flask and moreover, the microorganism cells-immobilizing carrier obtained above is added and thereafter, ZAIMOMONASU MOBIRISU IFO13756 is added to perform still-standing activation culture at 30° C. for 24 hr.

Moreover, the same activation culture is performed by using sellite (manufactured by WAKO JUNYAKU KOGYO Co., Ltd.) and chitin (manufactured by WAKO JUNYAKU KOGYO Co., Ltd.) as carriers for comparison.

After activation, the surface of each carrier is cleaned with distilled water and thereafter, activation fermentation liquid is replaced with a new culture medium to perform still-standing culture and compare ethanol concentrations as shown below. As a result, the granular carrier manufactured by embodiment 1 shows the highest ethanol concentration.

| Carrier | Ethanol concentration |
| --- | --- |
| Embodiment 1 | 7.5% |
| Sellite | 4.8% |
| Chitin | 4.1% |

Embodiment 2

After completely mixing 150 g of photo-curable resin ENTG-3800 (manufactured by KANSAI PAINT CO., LTD.) and 60 g of water, 6 g of polymerization initiator DAROCUR 1173 (manufactured by CIBA GEIGY GMBH) and 50 g of 2% sodium alginate solution are added and completely agitated to prepare a liquid composition. Then, a microorganism cells-immobilizing carrier having a specific gravity of 1.01 and a contact angle formed with n-paraffin of 10° is obtained by using a manufacturing system of the present invention.

A 3% calcium chloride solution is used as an aqueous medium containing metallic ions.

Then, 1 liter of the granular carrier prepared above and 500 ml of suspension of Saccharomyces cervisiae IFO0203 are added into a fluidized-bed-type bioreactor (capacity of 10 liter). Through the bioreactor, there is passed a culture medium, which has been prepared by adding glucose to five liters of culture medium GY-10 (comprising 1 g/l of yeast extract and 100 g/l of glucose) so that a glucose concentration may become 200 g/l, at a residence time of 15 hr and a passing velocity of vvm, and, thus, activation operation is performed for 24 hr. After activation is completed, continuous operation is performed at 30° C. for a residence time of 5 hr. Thus, ethanol is stably produced at a concentration of at least 70 g/l.

Embodiment 3

A microorganism cells-immobilizing granular carrier having a specific gravity of 1.01 is obtained by the same method as the case of embodiment 1 except to use a product obtained by adding 15 parts by weight of Zymomonas mobilis IFO 13756 to the liquid composition prepared in embodiment 1 as a liquid composition.

INDUSTRIAL APPLICABILITY

A microorganism cells-immobilizing carrier of the present invention has a small specific gravity of 1.00 to 1.20, in which the surface of the carrier is specified in a range of 2° to 30° in terms of a contact angle formed with n-paraffin. Therefore, microorganisms are easily attached to the surface and hardly removed from the surface. Therefore, when using the carrier to which microorganism cells are immobilized, it is possible to perform a stable microorganism reaction as shown by the above embodiments. Moreover, because a carrier of the present invention has a small specific gravity, the carrier can be easily applied to a fluidized-bed-type reactor.

Furthermore, according to a manufacturing system of the present invention, because ultraviolet radiation can be efficiently applied to a granular gel continuously moving in a solution, the system can be widely used as a method for manufacturing a lot of particulate matter.

We claim:

1. A microorganism cells-immobilizing granular carrier which has a surface suitable for the attachment of a microorganism, and which has a specific gravity of 1.00 to 1.20 and a contact angle of 2° to 30° formed between the carrier surface and n-paraffin, said carrier being characterized in that it is obtained by dripping a liquid composition containing (a) a hydrophilic photo-curable resin having at least two ethylenically unsaturated bonds in one molecule, (b) photopolymerization initiator, and (c) aqueous macromolecular polysaccharide capable of gelatinizing through contact with an alkaline metal ion or polyvalent metal ion, into an aqueous medium containing alkaline metal ions or polyvalent metal ions to gelatinize the composition into a granular form, and then irradiating the composition with active rays to be hardened.

2. A granular carrier according to claim 1, wherein a hydrophilic photo-curable resin (a) is a resin obtained by combining a compound having a photopolymerizable ethylenically-unsaturated group with the both ends of polyalkylene glycol.

3. A granular carrier according to claim 1, wherein a photopolymerization initiator (b) is selected from the group consisting of $\alpha$-carbonyls, acyloin ethers, polycyclic aromatic compounds, $\alpha$-substituted acyloins, and azoamide compounds.

4. A granular carrier according to claim 1, wherein a water-soluble macromolecular polysaccharide (c) is selected from the group consisting of alkaline metal salt of alginic acid and carageenan.

5. A granular carrier according to claim 1, wherein a polyvalent metal ion is alkaline earth metal ion.

6. A microorganism cells-immobilizing granular carrier according to claim 1, wherein a liquid composition contains microorganism cells.

7. A granular carrier manufacturing system comprising a gelatinizer for forming a granular gel by dripping a liquid composition containing (a) a hydrophilic photo-curable resin having at least two ethylenically unsaturated bonds in one molecule, (b) photopolymerization initiator, and (c) aqueous macromolecular polysaccharide capable of gelatinizing through contact with an alkaline metal ion or polyvalent metal ion, into an aqueous medium containing alkaline metal ions or polyvalent metal ions, and thus gelatinizing said composition into granular gel; and a light irradiator for forming a particulate matter by irradiating the granular gel formed by said gelatinizer with ultraviolet radiation and hardening a photo-curable resin in said granular gel; wherein said light irradiator is provided with a light source and a plurality of transparent tubes which are almost vertically arranged closely to said light source and in which said granular gel is moved.

8. A granular carrier manufacturing system according to claim 7, wherein said transparent tubes are arranged at positions of equal distances from said light source so as to surround said light source.

9. A granular carrier manufacturing system according to claim 7, wherein said transparent tubes are arranged in a line.

10. A granular carrier manufacturing system according to claim 7, wherein transparent tubes of a line are further arranged at positions where ultraviolet radiation can be directly applied through gaps between transparent tubes arranged in another line.

11. A granular carrier manufacturing system according to claim 9, wherein a plurality of said light sources are vertically arranged, the position of said light sources and that of transparent tubes being alternate with each other.

12. A granular carrier manufacturing system according to claim 7, wherein said light irradiator connects with a pump for moving said particulate matter and said aqueous medium.

13. A granular carrier manufacturing system according to claim 7, which is provided with a solid-liquid separator which separates said particulate matter and said aqueous medium, which have passed through said light irradiator from each other, sending said particulate matter to a recovery vessel, while sending said aqueous medium to a gelatinizer.

14. A granular carrier manufacturing system according to claim 7, wherein said liquid composition contains an enzyme or microorganism cells.

15. A granular carrier manufacturing system according to claim 10, wherein a plurality of said light sources are vertically arranged, the position of said light sources and that of transparent tubes being alternate with each other.

* * * * *